US 6,747,173 B2

(12) United States Patent
Gerkema et al.

(10) Patent No.: US 6,747,173 B2
(45) Date of Patent: Jun. 8, 2004

(54) METHOD FOR THE PREPARATION OF LACTIC ACID AND CALCIUM SULPHATE DIHYDRATE

(75) Inventors: Markus Gerkema, Breda (NL); Aldwin Korevaar, Giessenburg (NL); Damien Michel Andre Camelot, Rotterdam (NL); Jan Van Breugel, Woudrichem (NL); Geert-Jan Witkamp, Bergschenhoek (NL); Agusti CerdàBaro, Cerdanyola (ES)

(73) Assignee: Purac Biochem B.V. (NL)

( * ) Notice: Subject to any disclaimer, the term of this patent is extended or adjusted under 35 U.S.C. 154(b) by 0 days.

(21) Appl. No.: 10/230,420

(22) Filed: Aug. 29, 2002

(65) Prior Publication Data

US 2003/0125581 A1 Jul. 3, 2003

Related U.S. Application Data

(63) Continuation-in-part of application No. 09/941,660, filed on Aug. 30, 2001, now Pat. No. 6,632,966.

(30) Foreign Application Priority Data

Aug. 24, 2001 (NL) .............................................. 1018821

(51) Int. Cl.⁷ .............................................. C07C 59/08

(52) U.S. Cl. ....................................................... 562/589
(58) Field of Search .......................................... 562/589

(56) References Cited

FOREIGN PATENT DOCUMENTS

| EP | 0 406 550 A1 | 1/1991 |
|---|---|---|
| GB | 1162514 | 8/1969 |
| WO | WO 93/24410 | 12/1993 |
| WO | WO 01/25180 A1 | 4/2001 |
| WO | WO 01/27064 A1 | 4/2001 |

*Primary Examiner*—Paul J. Killos
(74) *Attorney, Agent, or Firm*—Gilberto M. Villacorta; Serge Sira; Katten Muchin Zavis Roseman

(57) ABSTRACT

The invention relates to a method for the preparation of lactic acid and calcium sulphate, in which (a) an aqueous solution that contains lactate is reacted with sulphuric acid at a temperature that is essentially higher than the transition temperature of calcium sulphate dihydrate ($CaSO_4.2H_2O$), with the formation of a mixture that contains calcium sulphate hemihydrate and lactic acid, (b) the mixture from step (a) is subjected to at least one recrystallisation step at a temperature that is essentially lower than the transition temperature of calcium sulphate dihydrate, with the formation of a precipitate of calcium sulphate dihydrate and an aqueous solution of lactic acid, and (c) the precipitate of calcium sulphate dihydrate is separated off from the aqueous solution of lactic acid.

9 Claims, 2 Drawing Sheets

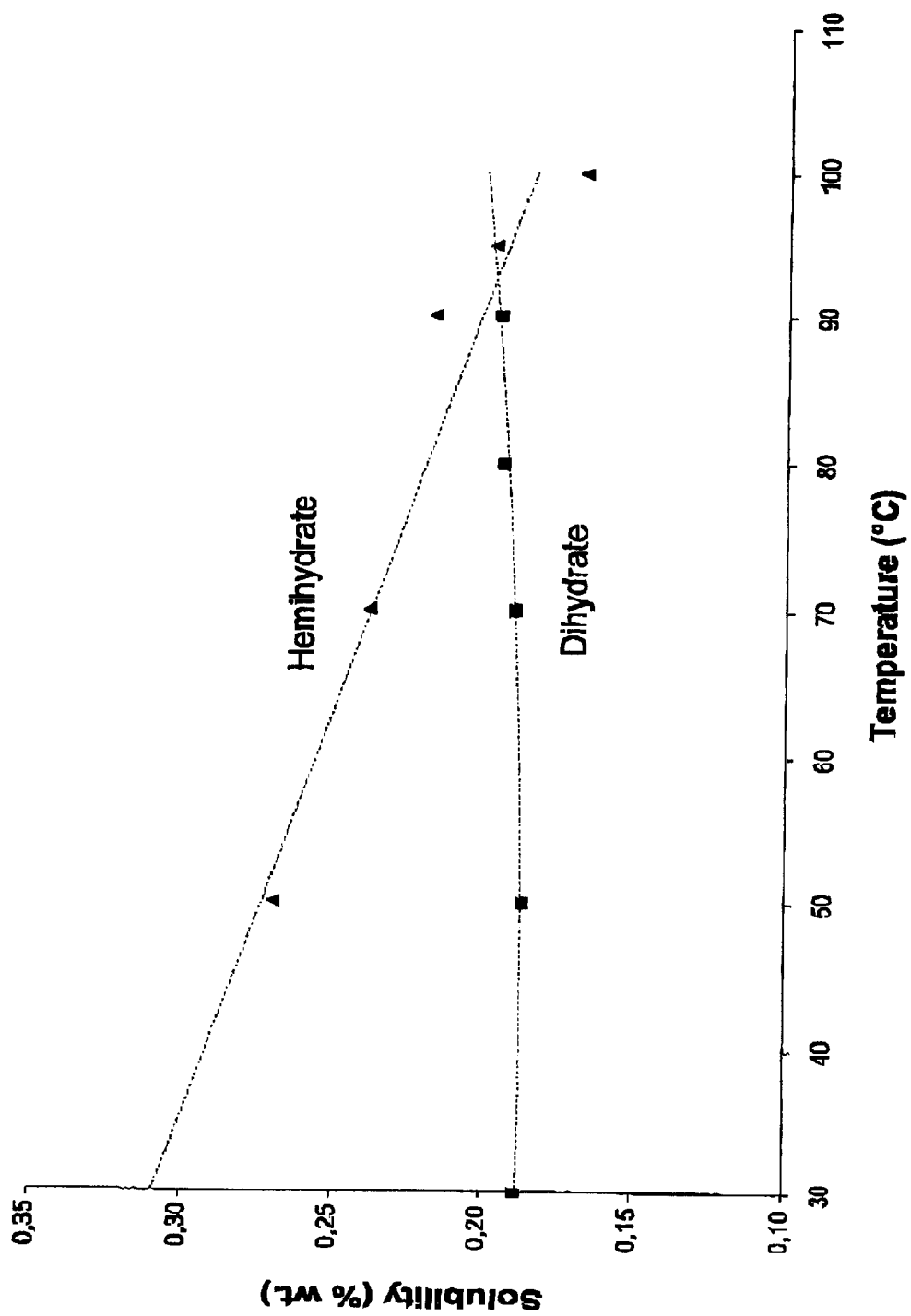

METHOD FOR THE PREPARATION OF LACTIC ACID AND CALCIUM SULPHATE DIHYDRATE

Figure 1:
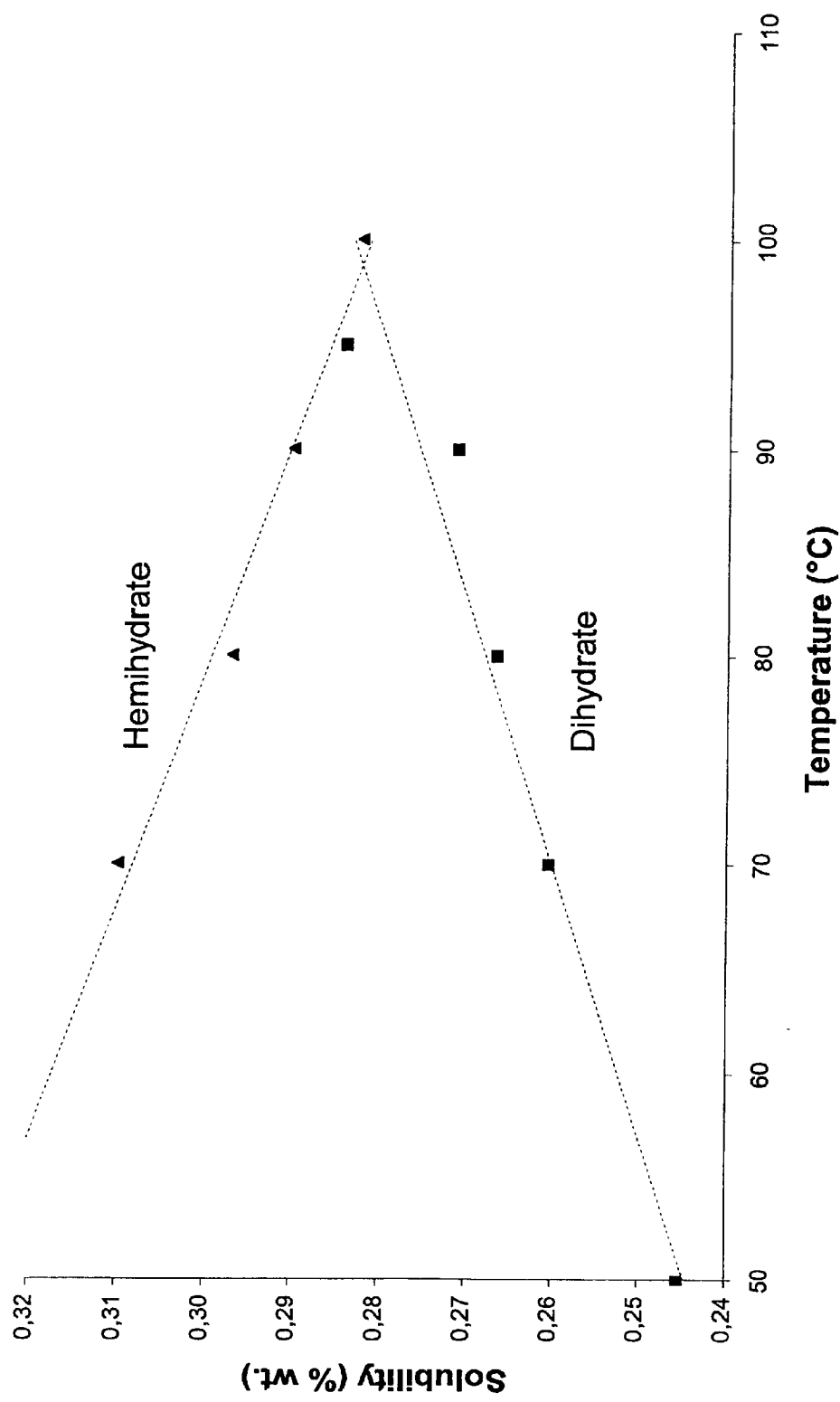

The present invention relates to the preparation of lactic acid and calcium sulphate.

It is known that (S)-lactic acid can be prepared by fermentation of sugars in water with the aid of microorganisms. Usually the pH of the fermentation medium is adjusted by adding calcium hydroxide, as a result of which calcium lactate is formed. The concentration of calcium lactate is approximately 275 g calcium lactate per litre or less. In order to be able to recover (S)-lactic acid in acid form from the fermentation medium, sulphuric acid, usually in concentrated form, is added with the formation of an aqueous solution of lactic acid and calcium sulphate dihydrate ($CaSO_4.2H_2O$), which is moderately soluble in water. The calcium sulphate dihydrate is separated from the aqueous solution of lactic acid by means of filtration, after which the aqueous solution of lactic acid is subjected to various subsequent steps in order ultimately to obtain pure lactic acid. The first step in the subsequent steps is often treatment with one or more ion exchangers. Examples for the purification and concentration of aqueous solutions of lactic acid are described, for example, in NL A 1 011 624, NL A 1 013 265 and NL A 1 013 682. It is, of course, also known that (R)-lactic acid can be prepared and purified in the manner described above.

The calcium sulphate that is obtained in the manner described above is mainly in the form of calcium sulphate dihydrate, which has the formula $CaSO_4.2H_2O$. In this description this compound is referred to as calcium sulphate dihydrate, in which context, however, this term must not be interpreted in such a restricted manner that it covers only pure $CaSO_4.2H_2O$. After all, it will be clear to those skilled in the art that other forms of calcium sulphate can be present.

Calcium sulphate dihydrate is used for various purposes, for example as a building material. A disadvantage of calcium sulphate dihydrate that is obtained according to the method described above is that it contains a large amount of free water. The free water content is as a rule approximately 25–35% by mass. Transport of this calcium sulphate dihydrate to other locations is therefore economically unattractive, in particular because appreciable quantities of water are transported. Another disadvantage of this calcium sulphate dihydrate is that it has a broad particle size distribution, is relatively highly coloured and contains a relatively large amount of impurities, which is disadvantageous for various end uses. In the case in question the calcium sulphate dihydrate also contains relatively large agglomerates of crystals, as a result of which the calcium sulphate dihydrate is difficult to filter (poor dewatering) and washing lactic acid out of the calcium sulphate dihydrate proceeds with difficulty and requires a large amount of wash water. Moreover, it has been found that other disadvantages arise on further treatment of the aqueous solution of lactic acid with one or more ion exchangers because there are relatively high concentrations of calcium and sulphate ions in the solution. As a result large quantities of regeneration agents are needed for regeneration of the ion exchangers, as a result of which the regeneration of the ion exchangers takes a great deal of time and is economically unattractive.

In WO 93/24410 a method is described for the preparation of α-calcium sulphate hemihydrate by reacting an aqueous solution of calcium lactate with sulphuric acid in an aqueous system at a temperature that is higher than the transition temperature of α-calcium sulphate hemihydrate/calcium sulphate. According to Example 1, the lactate concentration is 18% (m/m), the transition temperature being cited as 96.5±0.3° C. In the remainder of this description $CaSO_4.0.5H_2O$ will be referred to as calcium sulphate hemihydrate, in which context this term must not be interpreted in such a restricted manner that it covers only pure $CaSO_4.0.5H_2O$. After all, it will be clear to those skilled in the art that other forms of calcium sulphate can be present.

However, according to the present invention it has been found that this transition temperature is dependent on the calcium lactate concentration used and that at relatively low temperature the solubility of calcium sulphate hemihydrate is higher than that of calcium sulphate dihydrate. For instance, the transition temperature at a lactate concentration of approximately 50% (m/m) is approximately 92° C. Consequently, fewer calcium and sulphate ions remain in the aqueous solution at high calcium lactate concentration, with the result that the pollution of the ion exchangers is low and these have to regenerated less frequently.

British Patent 1 162 514 describes a method for the preparation of phosphoric acid and calcium sulphate from phosphate ore and sulphuric acid. If this preparation is carried out at high temperature, usually between 80° and 90° C., and with a high phosphoric acid concentration (higher than 30%), calcium sulphate is formed in the hemihydrate form ($CaSO_4.0.5H_2O$).

At lower temperatures (70° to 75° C.) and a low phosphoric acid concentration (20 to 25%) calcium sulphate dihydrate is formed. One of the disadvantages of this preparation in which calcium sulphate dihydrate is obtained is that inclusion of $CaHPO_4.2H_2O$ takes place in the calcium sulphate crystals formed, as a result of which impure calcium sulphate dihydrate is obtained and the yield of phosphoric acid is lower. This publication indicates that this disadvantage can be eliminated by carrying out the method in such a way that essentially calcium sulphate hemihydrate is formed, after which the calcium sulphate hemihydrate can be converted to calcium sulphate dihydrate by lowering the temperature and phosphate concentration. However, the calcium sulphate dihydrate thus obtained was still found to contain large quantities of phosphate. Another solution given was to isolate the calcium sulphate hemihydrate formed by means of filtration and then to recrystallise it in dilute phosphoric acid with the formation of calcium sulphate dihydrate. This, however, had the disadvantages that too early a conversion from the hemihydrate form to the dihydrate form took place, that this conversion took place under conditions which are unfavourable for the growth of dihydrate crystals and that the calcium sulphate dihydrate finally formed still contained large amounts of phosphate.

The method according to British Patent 1 162 514 comprises the treatment of phosphate ore with sulphuric acid or a mixture of phosphoric acid and sulphuric acid at such a temperature, preferably from 75° to 105° C., that a suspension of crystals of $CaSO_4.0.5H_2O$ (calcium sulphate hemihydrate) in a concentrated phosphoric acid solution is formed. The crystals are then separated off from the concentrated phosphoric acid solution and then washed with an aqueous solution of sulphuric acid or of sulphuric acid and phosphoric acid under conditions such that the calcium sulphate hemihydrate crystals are not converted into a different crystal form, for example calcium sulphate dihydrate. In a subsequent step the calcium sulphate hemihydrate crystals are recrystallised from an aqueous solution that contains 2 to 25% by mass sulphuric acid and less than 20% by mass phosphoric acid at a temperature that is lower than 90° C.

It thus appears that the problems that are associated with the preparation of inorganic acids such as phosphoric acid are completely different to those which are associated with the preparation of organic acids such as lactic acid.

BRIEF DESCRIPTION OF THE FIGURE LEGENDS

FIG. 1. The solubility of the calcium sulphate dihydrate and calcium sulphate hemihydrate salts as a function of the temperature (20% weight lactic acid).

FIG. 2. The solubility of the calcium sulphate dihydrate and calcium suplhate hemihydrate salts as a function of the temperature (50% weight lactic acid).

The present invention, however, provides a solution to the problems which are associated with the preparation of an aqueous solution of lactic acid. The invention therefore also relates in particular to a method for the preparation of lactic acid and calcium sulphate, in which:

(a) an aqueous solution that contains lactate is reacted with sulphuric acid at a temperature that is essentially higher than the transition temperature of calcium sulphate dihydrate/calcium sulphate hemihydrate ($CaSO_4.2H_2O/CaSO_4.0.5H_2O$), to form a mixture that contains calcium sulphate hemihydrate and lactic acid, (b) the mixture from step (a) is subjected to at least one recrystallisation step at a temperature that is essentially lower than the transition temperature of calcium sulphate dihydrate/calcium sulphate hemihydrate, to form a precipitate of calcium sulphate dihydrate and an aqueous solution of lactic acid, and (c) the precipitate of calcium sulphate dihydrate is separated off from the aqueous solution of lactic acid.

According to the invention the aqueous solution of lactate (and possibly lactic acid, for example if the fermentation is carried out at a low pH) preferably contains 0.1 to 70% by mass lactate, more preferentially 10 to 60% by mass and in particular 15 to 50% by mass. These quantities have been calculated based on the total quantity of [lactate+lactic acid] in the aqueous solution. If the aqueous solution that is obtained after fermentation has too low a lactate concentration, the solution can be concentrated, before it is treated with sulphuric acid, by means of evaporation of water or by reverse osmosis or with the aid of membranes (pervaporation) as is described, for example, in WO 00/56693, WO 01/25180, WO 01/27064 and WO 01/38283, which are incorporated here for reference. The sulphuric acid preferably contains 30–98% by mass pure sulphuric acid. Oleum can also be used instead of this sulphuric acid. In particular, the sulphuric acid contains at least 95% by mass pure sulphuric acid.

It has been found that the temperature at which steps (a) and (b) are carried out is dependent on the lactate concentration in the aqueous solution. This temperature is lower at higher lactate concentration. According to the invention it is therefore preferable to work at a relatively high lactate concentration, which means that according to this embodiment the lactate concentration (based on the total amount of [lactate+lactic acid] in the aqueous solution) is preferably 15 to 50% (m/m) and in particular 20 to 50% (m/m). This preferred embodiment has the additional advantage that fewer sugars decompose as a result of thermal degradation during step (a). Decomposition of sugars gives rise to the formation of products that are disadvantageous for the colour characteristics of the lactic acid finally to be obtained. Furthermore, fewer calcium sulphate salts (dihydrate, hemihydrate and the like) remain behind in the aqueous solution of lactic acid, as a result of which the ion exchangers are less polluted, or are even no longer required, in the subsequent step for purification and concentration of the aqueous solution of lactic acid.

According to the invention, step (b) preferably comprises at least two steps, more preferably the first step being carried out at a temperature that is higher than the temperature at which the second step is carried out.

The calcium sulphate dihydrate obtained using the present method contains less than 25% by mass free water, more preferentially less that 15% by mass and in particular less than 12% by mass, based on the total quantity of calcium sulphate dihydrate. Furthermore, the calcium sulphate dihydrate has a narrower particle size distribution and fewer crystal agglomerates than does the calcium sulphate dihydrate according to the prior art and consequently has better filterability and is better able to be washed out.

The method according to the present invention can be carried out batchwise or continuously and is preferably carried out continuously. The separation step (c) can, for example, be carried out by means of filtration. However, according to the invention it is preferable that the calcium sulphate dihydrate is separated off from the aqueous solution of lactic acid by means of cyclone separation prior to the filtration, as a result of which a better particle size distribution can be obtained.

EXAMPLE 1

The solubility of calcium sulphate dihydrate and calcium sulphate hemihydrate was determined at various concentrations as a function of the temperature. Stock solutions of lactic acid were prepared by diluting an aqueous solution of 90% lactic acid of pharmaceutical quality (PH 90, batch number 2000200003) with water to 20% (m/m) and 50% (m/m), respectively, and heating at 80° C. for four days. 50 ml samples of these solutions were heated for 30 minutes at various temperatures, after which 10 g of either calcium sulphate dihydrate or calcium sulphate hemihydrate was added, a suspension being formed. 20 ml samples of the suspensions were taken after 15 and after 20 minutes and these were filtered through a G4 glass filter. The mother liquor was analysed to determine the $Ca^{2+}$ content. The calcium sulphate crystals filtered off were washed twice with 20 ml acetone and twice with 10 ml acetone and finally dried at 30° C. to remove any residual acetone. The water of crystallisation content was then determined by drying the crystals for at least 16 hours at 160° C. and determining the loss in weight. The water of crystallisation in calcium sulphate hemihydrate was found to be 6.2% (m/m) and that in calcium sulphate dihydrate was found to be 20.9% (m/m). The solubilities of the calcium sulphate salts are given in Table 1 and have been plotted against the temperature (see FIGS. 1 and 2).

The free water and water of crystallisation contents were determined using a Mettler Toledo, HR Halogen Moisture. For these determinations a few grams of sample were placed in a dish and the dish was placed in the equipment. The sample was automatically dried until there was no further loss in weight. The water content was automatically calculated from the loss in weight. The set temperature for determination of the water of crystallisation content was 130° C. The set temperature for determination of the free water content was 60° C.

TABLE 1

| Temperature (° C.) | $Ca^{2+}$ (ppm) | $CaSO_4.0.5H_2O$ (% (m/m)) |
|---|---|---|
| Calcium sulphate hemihydrate (20% (m/m) lactic acid) | | |
| 30 | — | — |
| 50 | — | — |
| 70 | 854 | 0.310 |
| 80 | 818 | 0.297 |
| 90 | 799 | 0.290 |
| 95 | — | — |
| 100 | 778 | 0.282 |
| Calcium sulphate hemihydrate (50% (m/m) lactic acid) | | |
| 30 | — | — |
| 50 | 742 | 0.269 |
| 70 | 655 | 0.238 |
| 80 | — | — |
| 90 | 597 | 0.217 |
| 95 | 542 | 0.197 |
| 100 | — | — |

| Temperature (° C.) | $Ca^{2+}$ (ppm) | $CaSO_4.2H_2O$ (% (m/m)) |
|---|---|---|
| Calcium sulphate dihydrate (20% (m/m) lactic acid) | | |
| 30 | — | — |
| 50 | 570 | 0.245 |
| 70 | 605 | 0.260 |
| 80 | 619 | 0.266 |
| 90 | 630 | 0.271 |
| 95 | 660 | 0.284 |
| 100 | — | — |
| Calcium sulphate dihydrate (50% (m/m) lactic acid) | | |
| 30 | 437 | 0.188 |
| 50 | 432 | 0.186 |
| 70 | 440 | 0.189 |
| 80 | 450 | 0.194 |
| 90 | 452 | 0.195 |
| 95 | — | — |
| 100 | — | — |

EXAMPLE 2

In a double-walled reaction vessel with a volume of 3 litres that was provided with a stirrer (stirrer speed 600 rpm), an aqueous solution that contained 34.01% by mass calcium lactate (the temperature of the solution was 95° C.; feed rate 30.57 ml/min) was continuously acidified with concentrated sulphuric acid (96%; feed rate 3.0 to 3.1 ml/min) at a temperature of 90° C., more than 95.7% (m/m) $CaSO_4.0.5H_2O$ being formed. The reaction was controlled by measuring the electrical conductivity (minimum 10.0 and maximum 14.5 mS/cm). The residence time in the reaction vessel was approximately 75 minutes. The reaction mixture was then fed successively to two 5 litre double-walled crystallisation vessels which were provided with a stirrer (crystallisation vessel 1: T=80° C., stirrer speed 400 rpm; crystallisation vessel 2: T=80° C., stirrer speed 400 rpm). The results that were obtained during the experiment are given in Table 2 below. The analytical results for the dihydrate crystals obtained after the second step and for the aqueous lactic acid solution are given in Table 3.

TABLE 2

(Crystallisation vessel 2)

| Time (hours) | Water of crystallisation (% (m/m)) | Dihydrate (% (m/m)) |
|---|---|---|
| 0 | 20.15 | 94.90 |
| 1 | 20.17 | 95.03 |
| 3 | 20.19 | 95.17 |
| 4 | 20.20 | 95.24 |
| 5 | 20.43 | 96.80 |
| 6 | 20.34 | 96.19 |
| 7 | 20.29 | 95.85 |
| 8 | 20.09 | 94.49 |
| 9 | 20.29 | 95.85 |
| 10 | 20.29 | 95.85 |
| 11 | 20.15 | 94.90 |

TABLE 3

| Lactic acid solution | |
|---|---|
| Free acid concentration | 35.58% (m/m) lactic acid |
| $[Ca^{2+}]$ | 0.13% (m/m) |
| $[SO_4^{2-}]$ | 0.04% (m/m) |
| Dihydrate | |
| Free water (average) | 8.26% (m/m) |
| Water of crystallisation (average) | 20.35% (m/m) |

EXAMPLE 3

In a double-walled reaction vessel with a volume of 3 litres that was provided with a stirrer (stirrer speed 800 rpm), an aqueous solution that contained 50% by mass calcium lactate (the temperature of the solution was 83° to 85° C.; feed rate 28 ml/min) was continuously acidified with concentrated sulphuric acid (96%; feed rate 4.0 to 4.3 ml/min) at a temperature of 90° C., more than 97.5% (m/m) $CaSO_4.0.5H_2O$ being formed. The reaction was controlled by measuring the electrical conductivity (minimum 5.4 and maximum 5.80 mS/cm). The residence time in the reaction vessel was approximately 62 minutes. The reaction mixture was then fed successively to two 5 litre double-walled crystallisation vessels which were provided with a stirrer (crystallisation vessel 1: T=62° C., stirrer speed 300 rpm; crystallisation vessel 2: T=60° C., stirrer speed 300 rpm). The results that were obtained during the experiment are given in Table 4 below. The analytical results for the dihydrate crystals obtained after the second crystallisation and for the aqueous lactic acid solution are given in Table 5.

TABLE 4

(Crystallisation vessel 2)

| Time (hours) | Water of crystallisation (% (m/m)) | Dihydrate (% (m/m)) |
| --- | --- | --- |
| 0 | 20.47 | 97.1 |
| 1 | 20.40 | 96.6 |
| 3 | 20.54 | 97.6 |
| 5 | 20.63 | 98.2 |
| 6 | 20.68 | 98.? |
| 7 | 20.68 | 98.5 |
| 8.5 | 20.73 | 98.8 |
| 10 | 20.74 | 98.9 |

TABLE 5

| Dihydrate | |
| --- | --- |
| Free water (average) | 10.80% (m/m) |
| Water of crystallisation (average) | 20.5% (m/m) |

It can be seen from Example 3 that at a higher calcium lactate concentration and lower recrystallisation temperatures calcium sulphate dihydrate crystals are obtained which have a free water content of no more than about 10% by mass, whilst with the conventional method calcium sulphate dihydrate crystals are obtained which have a free water content of approximately 25 to 35% by mass.

What is claimed is:

1. A method of preparing of lactic acid and calcium sulphate, comprising:
    (a) allowing an aqueous solution that contains lactate to react with sulphuric acid at a temperature that is essentially higher than the transition temperature of calcium sulphate dihydrate/ calcium sulphate hemihydrate ($CaSO_4.2H_2O/CaSO_4. 0.5 H_2O$), to form a mixture that contains calcium sulphate hemihydrate and lactic acid,
    (b) subjecting the mixture from step (a) to at least one recrystallisation step at a temperature that is lower than the transition temperature of calcium sulphate dihydrate/calcium sulphate hemihydrate, to form a precipitate of calcium sulphate dihydrate and an aqueous solution of lactic acid, and
    (c) separating the precipitate of calcium sulphate dihydrate from the aqueous solution of lactic acid.

2. The method of claim 1, wherein the aqueous solution of lactate contains 0.1 to 70% by mass calcium lactate.

3. The method of claim 1, wherein the sulphuric acid comprises at least 30 to 98% by mass pure sulphuric acid.

4. The method of claim 1, wherein step (b) includes at least two recrystallisation steps.

5. The method of claim 1, wherein the first recrystallisation step is conducted at a higher temperature than the second recrystallisation step.

6. The method of claim 1, wherein the calcium sulphate hemihydrate from step (a) contains $CaSO_4.0.5H_2O$.

7. The method of claim 1, wherein the calcium sulphate according to step (b) comprises essentially calcium sulphate dihydrate ($CaSO_4.2.0H_2O$).

8. The method of claim 7, wherein the calcium sulphate dihydrate according to step (c) contains less than 25% by mass free water.

9. The method of claim 1, wherein the aqueous solution of lactate is obtained by fermentation and is then concentrated before the solution is treated with sulphuric acid.

* * * * *